US009890097B2

(12) United States Patent
Bonnet et al.

(10) Patent No.: US 9,890,097 B2
(45) Date of Patent: Feb. 13, 2018

(54) METHOD OF OBTAINING A COMBINATION OF Z AND E STEREOISOMERS OF 1-CHLORO-3,3,3-TRIFLUOROPROPENE

(71) Applicant: Arkema Inc., King of Prussia, PA (US)

(72) Inventors: Philippe Bonnet, Lyons (FR); Maher Y. Elsheikh, Wayne, PA (US)

(73) Assignee: Arkema Inc., King of Prussia, PA (US)

( * ) Notice: Subject to any disclaimer, the term of this patent is extended or adjusted under 35 U.S.C. 154(b) by 0 days.

(21) Appl. No.: 14/870,160

(22) Filed: Sep. 30, 2015

(65) Prior Publication Data

US 2016/0016868 A1  Jan. 21, 2016

Related U.S. Application Data

(60) Continuation of application No. 13/939,233, filed on Jul. 11, 2013, now Pat. No. 9,181,154, which is a division of application No. 12/667,115, filed as application No. PCT/US2008/075165 on Sep. 4, 2008, now abandoned.

(60) Provisional application No. 60/972,037, filed on Sep. 13, 2007.

(51) Int. Cl.

| C07C 17/383 | (2006.01) |
| C07C 21/18 | (2006.01) |
| C07C 17/358 | (2006.01) |
| C07C 17/38 | (2006.01) |
| C07C 17/386 | (2006.01) |
| C07C 17/389 | (2006.01) |
| C08J 9/14 | (2006.01) |
| C09K 3/30 | (2006.01) |
| C09K 5/04 | (2006.01) |

(52) U.S. Cl.
CPC ............ *C07C 17/358* (2013.01); *C07C 17/38* (2013.01); *C07C 17/383* (2013.01); *C07C 17/386* (2013.01); *C07C 17/389* (2013.01); *C07C 21/18* (2013.01); *C08J 9/146* (2013.01); *C09K 3/30* (2013.01); *C09K 5/045* (2013.01); *C09K 2205/126* (2013.01); *C09K 2205/22* (2013.01); *Y02P 20/127* (2015.11)

(58) Field of Classification Search
CPC ..... C07C 17/358; C07C 17/38; C07C 17/383; C07C 17/389; C07C 21/18
See application file for complete search history.

(56) References Cited

U.S. PATENT DOCUMENTS

| 5,391,791 A | 2/1995 | Dubois et al. |
| 5,446,217 A | 8/1995 | Van Der Puv et al. |
| 5,986,151 A | 11/1999 | Van Der Puv |
| 6,120,652 A | 9/2000 | Hibino et al. |
| 6,124,510 A | 9/2000 | Elsheikh et al. |
| 6,194,619 B1 | 2/2001 | Rao et al. |
| 7,179,949 B2 | 2/2007 | Wilmet |
| 7,485,760 B2* | 2/2009 | Wang ..................... C01B 7/191 570/156 |
| 2002/0019521 A1 | 2/2002 | Orr et al. |
| 2005/0119512 A1* | 6/2005 | Du Boisson ............ C07C 17/25 570/136 |
| 2007/0100174 A1 | 5/2007 | Miller et al. |
| 2007/0108403 A1 | 5/2007 | Sievert et al. |
| 2010/0032610 A1 | 2/2010 | Nappa et al. |
| 2010/0197979 A1 | 8/2010 | Nappa |

FOREIGN PATENT DOCUMENTS

| EP | 0 939 071 A1 | 9/1999 |
| WO | WO 2005/012212 A2 | 2/2005 |
| WO | WO 2005/014512 A2 | 2/2005 |
| WO | WO 2005/105947 A2 | 11/2005 |
| WO | WO 2006/094303 A2 | 9/2006 |
| WO | WO 2007/002625 A2 | 1/2007 |
| WO | WO 2007/002703 A2 | 1/2007 |

OTHER PUBLICATIONS

Specification of U.S. Appl. No. 60/839,874, filed Aug. 24, 2006, pp. 1-17.*
Quan (Quan, H-D. et al. "Preparation of 1,1,1,3,3-pentafluoropropane (HFC-245fa) by using a SbF5-attached catalyst" Journal of Fluorine Chemistry 128 (2007) 190-195; Available online Dec. 10, 2006) (Year: 2006).*
Burton, D.J. et al., Preparation of E-1,2,3,3,3-Pentafluoropropene, Z-1,2,3,3,3-Pentafluoropropene and E-I-Iodopentafluoropropene, Journal of Fluorine Chemistry, vol. 44, No. 1, Jul. 1, 1989, pp. 167-174.
Sianesi, D. et al., Fluoro olefins-Cis and Trans-1,2,3,3,3-Pentafluoropropylene, Annali. Di Chimica, Societa Chemica Italiana, vol. 55, No. 8-9. Jan. 1, 1966, pp. 850-861.
Haszeldine, R.N. et al. Addition of Free Radiclas to Un saturated Systems, Part XXI, Reactions of 1H-Pentafluoropropene with Bromine, Hydrogen Bromide and Trifluorodomethan under Free-Radical Condition, J. of the Chemical Society, GB, Jan. 1, 1974, pp. 1303-1307.
Quan, H., et al., Preparation of 1,1,1,3,3-Pentafluoropropane (HCF-245fa) by Using a SbF5-Attached Catalys, Journal of Fluorine Chemistry, 128, (2007), 99 , pp. 190-195.

* cited by examiner

*Primary Examiner* — Medhanit W Bahta
(74) *Attorney, Agent, or Firm* — Steven D. Boyd

(57) ABSTRACT

Disclosed are the combinations containing Z and E stereoisomers of hydrofluoroolefins where the more toxic isomer is less than about 30% weight of the combination (vs the sum of Z+E), to minimize the toxicity impact in the applications they will be used for such as cooling and heat fluids, foams blowing agents or solvents. Also disclosed are means to obtain combinations containing Z and E stereoisomers of hydrofluoroolefins.

1 Claim, No Drawings

METHOD OF OBTAINING A COMBINATION OF Z AND E STEREOISOMERS OF 1-CHLORO-3,3,3-TRIFLUOROPROPENE

The present application claims priority to and is a continuation of U.S. application Ser. No. 13/939,233 filed Jul. 11, 2013; which claims priority to and is a divisional application of U.S. application Ser. No. 12/667,115 filed Dec. 29, 2009, abandoned, which claims priority to International application serial number PCT/US08/75165 filed Sep. 4, 2008 which designated the United States; which claims priority to U.S. provisional application Ser. No. 60/972,037 filed Sep. 13, 2007.

FIELD OF THE INVENTION

The present invention relates to compositions containing a combination of Z and E stereoisomers of hydrofluoroolefins. The present invention also relates to means to obtain the compositions. The compositions of the present invention are useful in processes for producing cooling or heat, as heat transfer fluids, refrigerants, foam blowing agents, aerosol propellants, fire suppression, extinguishing agents and solvent applications for metal degreasing and dewatering agent.

BACKGROUND OF THE INVENTION

The Montreal Protocol for the protection of the ozone layer, mandate the phase out of the use of chlorofluorocarbons (CFCs). Materials more "friendly" to the ozone layer, such as hydrofluorocarbons (MFCs) eg HFC-134a replaced chlorofluorocarbons. The latter compounds have proven to be green house gases, causing global warming and were regulated by the Kyoto Protocol on Climate Change. The emerging replacement materials, hydrofluoropropene, were shown to be environmentally acceptable ie has zero ozone depletion potential (ODP) and acceptable low GWP.

Currently proposed replacement refrigerants for hydrofluorocarbons such as HFC-134a include HFC-152a, pure hydrocarbons such as butane or propane, or "natural" refrigerants such as $CO_2$. Many of these suggested replacements are, flammable, and/or have low energy efficiency. Therefore, new alternative refrigerants are being sought. Fluoroolefin materials such as hydrofluoropropene have generated interest as replacements for HFCs. The inherent chemical instability of these materials in the lower atmosphere provides the low global warning potential and zero or near zero ozone depletion properties desired. However, such inherent instability is believed to also impact their toxicity. In particular, the Z isomer will be much more active towards oxygen compared to the E isomer.

The object of the present invention is to provide novel compositions that can serve as refrigerant and heat transfer fluids as well as blowing agents, solvent cleaners etc. that provide unique characteristics to meet the demands of low or zero ozone depletion potential, lower global warming potential and low toxicity.

SUMMARY OF THE INVENTION

The present invention is directed toward combinations containing Z and E stereoisomers of hydrofluoroolefins where the more toxic isomer is less than 30% weight of the combination (vs the sum of Z+E), to minimize the toxicity impact in the applications they will be used for such as cooling and heat fluids, foams blowing agents or solvents. The invention is also directed toward means to obtain these combinations.

DESCRIPTION OF THE INVENTION

Hydrofluoroolefins have been proposed as heat transfer fluids as well as blowing agents, solvent cleaners etc. which exhibit a low global warming potential and zero ozone depletion value. The low global warming potential is a result of the atmospheric degradation of the hydro fluoroolefins, typically in just a few days. The fast atmospheric degradation of hydrofluoroolefins is related to reactivitiy with OH radicals.

Toxicity of hydrofluoroolefins varies between the geometric isomers.

Hydrofluoroolefins, which can exist as Z and E isomers are of particular interest include:
  F1225 ye (1,2,3,3,3-pentafluoropropene) (Z and E isomers) and
  F1234 ze (1,3,3,3-tetrafluoropeopene) (Z and E isomers)
  F1233zd (1-chloro-3,3,3-trifluoropropene) (Z and E isomers)

From a reactivity point of view, the more sterically hindered isomer is believed to be more reactive and therefore likely more toxic. A preferred ratio of Z and E isomers is less than about 30% weight of the combination of the more toxic isomer (vs the sum of Z+E) and even more preferably less than about 10% of the more toxic isomer. The most preferred ratio is less than about 1% of the more toxic isomer (vs the sum Z+E).

For F1225 ye (1,2,3,3,3-pentafluoropropene), a preferred ratio of Z and E isomers is less than about 30% weight of the combination of the E isomer (vs the sum of Z+E) and even more preferably less than about 10% of the E isomer. The most preferred ratio is less than about 1% of the E isomer (vs the sum Z+E).

For F1234 ze (1,3,3,3-tetrafluoropeopene), a preferred ratio of Z and E isomers is less than about 30% weight of the combination of the Z isomer (vs the sum of Z+E) and even more preferably less than about 10% of the Z isomer. The most preferred ratio is less than about 1% of the Z isomer (vs the sum Z+E).

For F1233zd (1-chloro-3,3,3-trifluoropropene), a preferred ration of Z and E isomers is less than about 30% weight of the combination of the Z isomer (vs. the sum of Z+E) and even more preferably less than about 10% of the Z isomer. The most preferred ratio is less than about 1% of the Z isomer (vs. the sum Z+E).The combinations of the present invention can also further include additional low global warming potential and low or zero ozone depletion value materials including but not limited to hydrocarbons such as pentane or cyclopentane, $CO_2$, hydrofluorocarbons such as difluoromethane (HFC-32), 1,1,1,3 tetrafluoroethane (HFC-134a), pentafluoroethane (HFC-125) and 1,1-difluoroethane (HFC-152a); and hydrochloroalkenes such as t-1, 2-dichloroethylene (1,2-DCE).

Different technologies can be used to separate stereoisomers to obtain the combinations of the present invention:
  Distillation, when boiling points of isomers are sufficiently different
  Reactive distillation based on the difference of reactivity of the isomers vs hydrogenation on chlorination (but not limited to that) followed by distillation of the products of reaction Catalytic isomerization of Z isomers to E isomers using a strong Lewis acid such as $SbF_5$ and a high surface area fluorinated alumina or activated carbon catalyst Extraction or extractive distillation with a third solvent, based of the difference of affinity of the isomers vs the solvent, the third solvent could be but is not limited to chlorinated C1, C2 and C3 solvents (CCl4, CCl3H, CH2Cl2, CHCl2-CHCl2, CCl3-CH3, CCl2=CCl2, CHCl=CHCl, CHCl=CCl2 . . . ), fluorinated or perfluorinated solvents (HFC, Hydrofluoroethers, PFC), oxygenated solvents such alcohols or ethers, N containing solvents such as amines, C1 to C10 hydrocarbons such as isobutane, butane, propane, pentane, isopentane hexane . . . .

Separation on solids beds based on difference of absorption of each isomer, the solids could be (but are not limited to) molecular sieves, alumina, carbon sieves, zeolites and the like.

Membrane separation technology, which allow for the selective passage of one isomer and retaining the other isomer.

1. Mobil Air Conditions (MAC) and Other Refrigerant Applications:

For MAC applications the preferred boiling point (bp) of the low GWP refrigerants is between −10 to −40+ C. Refrigerant must be chemically stable during applications eg, doesn't react with active metal in the system such as aluminum, copper or iron, soluble and compatible with refrigerant oil.

The combinations containing Z and E stereoisomers of hydrofluoroolefins of the present invention have been found effective as replacements for high GWP (global warming potential) refrigerant in refrigeration, air-conditioning, or heat pump systems. Conventional high GWP refrigerants in such systems include materials such as R134a, R22, R245fa, R114, R236fa, R124, R410A, R407C, R417A, R422A, R507A, and R404A. The combinations containing Z and E stereoisomers of hydrofluoroolefins of the present invention are effective working fluids in refrigeration, air-conditioning, or heat pump apparatus that uses, used or is designed to use conventional high GWP refrigerants.

Vapor-compression refrigeration, air-conditioning, or heat pump systems include an evaporator, a compressor, a condenser, and an expansion device. A vapor-compression cycle re-uses refrigerant in multiple steps producing a cooling effect in one step and a heating effect in a different step. The cycle can be described simply as follows: liquid refrigerant enters an evaporator through an expansion device, and the liquid refrigerant boils in the evaporator at a low temperature to form a gas and produce cooling. The low-pressure gas enters a compressor where the gas is compressed to raise its pressure and temperature. The higher-pressure (compressed) gaseous refrigerant then enters the condenser in which the refrigerant condenses and discharges its heat to the environment. The refrigerant returns to the expansion device through which the liquid expands from the higher-pressure level in the condenser to the low-pressure level in the evaporator, thus repeating the cycle.

As used herein, mobile refrigeration apparatus or mobile air-conditioning (MAC) apparatus refers to any refrigeration or air-conditioning apparatus incorporated into a transportation unit for the road, rail, sea or air. The present invention is particularly useful for road transport refrigerating or air-conditioning apparatus, such as automobile air-conditioning apparatus or refrigerated road transport equipment.

The combinations containing Z and E stereoisomers of hydrofluoroolefins of the present invention may also be useful in stationary air-conditioning and heat pumps, e.g. chillers, high temperature heat pumps, residential and light commercial and commercial air-conditioning systems. In stationary refrigeration applications, the present compositions may be useful in equipment such as domestic refrigerators, ice machines, walk-in and reach-in coolers and freezers, and supermarket systems.

When used as refrigerants, the combinations containing Z and E stereoisomers of hydro fluoroolefins of the present invention typically will include refrigeration lubricants, i.e. those lubricants suitable for use with refrigeration, air-conditioning, or heat pump apparatus. Among these lubricants are those conventionally used in compression refrigeration apparatus utilizing chlorofluorocarbon refrigerants. Such lubricants and their properties are discussed in the 1990 ASHRAE Handbook, Refrigeration Systems and Applications, chapter 8, titled "Lubricants in Refrigeration Systems". Lubricants of the present invention may comprise those commonly known as "mineral oils" in the field of compression refrigeration lubrication. Mineral oils comprise paraffins (i.e. straight-chain and branched-carbon-chain, saturated hydrocarbons), naphthenes (i.e. cyclic paraffins) and aromatics (i.e. unsaturated, cyclic hydrocarbons containing one or more rings characterized by alternating double bonds). Lubricants of the present invention further comprise those commonly known as "synthetic oils" in the field of compression refrigeration lubrication. Synthetic oils comprise alkylaryls (i.e. linear and branched alkyl alkylbenzenes), synthetic paraffins and napthenes, and poly(alphaolefins). Lubricants of the present invention further comprise those that have been designed for use with hydrofluorocarbon refrigerants and are miscible with refrigerants of the present invention under compression refrigeration, air-conditioning, or heat pump apparatus operating conditions. Such lubricants include, but are not limited to, polyol esters (POEs) such as Castrol® 100 (Castrol, United Kingdom), polyalkylene glycols (PAGs) such as RL-488A from Dow (Dow Chemical, Midland, Mich.), and polyvinyl ethers (PVEs). These lubricants are readily available from various commercial sources.

2. Blowing Agents

For polyurethane blowing applications the preferred combinations of the present invention will typically have boiling points between about −40° C. to 60° C. and be compatible with the A side, the B side or both and typically are liquid at atmospheric pressure from about 10° C. to 50° C. and more preferably 30° C. to 40° C. and provide a foam with good dimensional stability. The combinations have a low thermal conductivity and provide a foam with low thermal conductivity.

For the production of thermoplastic foams, the preferred combinations of the present invention will have boiling points less than the melt and/or glass transition temperature of the polymer resin, typically less than about 100° C., preferably between about −40° C. to about 10° C.

The process for preparing a foamed thermoplastic product is as follows: Prepare a foamable polymer composition by blending together components comprising foamable polymer composition in any order. Typically, prepare a foamable polymer composition by plasticizing a polymer resin and then blending in components of a blowing agent composition at an initial pressure. A common process of plasticizing a polymer resin is heat plasticization, which involves heating a polymer resin enough to soften it sufficiently to blend in a blowing agent composition. Generally, heat plasticization involves heating a thermoplastic polymer resin near or above its glass transition temperature (Tg), or melt temperature (Tm) for crystalline polymers.

A foamable polymer composition can contain additional additives such as nucleating agents, cell-controlling agents, dyes, pigments, fillers, antioxidants, extrusion aids, stabilizing agents, antistatic agents, fire retardants, IR attenuating agents and thermally insulating additives. Nucleating agents include, among others, materials such as talc, calcium carbonate, sodium benzoate, and chemical blowing agents such azodicarbonamide or sodium bicarbonate and citric acid. IR attenuating agents and thermally insulating additives include carbon black, graphite, silicon, dioxide, metal flake or powder, among others. Flame retardants can include, among others, brominated materials such as hexabromocyclodecane and polybrominated biphenyl ether.

Foam preparation processes of the present invention include hatch, semi-batch, and continuous processes. Batch processes involve preparation of at least one portion of the foamable polymer composition in a storable state and then using that portion of foamable polymer composition at some future point in time to prepare a foam.

A semi-batch process involves preparing at least a portion of a foamable polymer composition and intermittently expanding that foamable polymer composition into a foam all in a single process. For example, U.S. Pat. No. 4,323,528, herein incorporated by reference, discloses a process for making polyolefin foams via an accumulating extrusion process. The process comprises: 1) mixing a thermoplastic material and a blowing agent composition to form a foamable polymer composition; 2) extruding the foamable polymer composition into a holding zone maintained at a temperature and pressure which does not allow the foamable polymer composition to foam; the holding zone has a die defining an orifice opening into a zone of lower pressure at which the foamable polymer composition foams and an openable gate closing the die orifice; 3) periodically opening the gate while substantially concurrently applying mechanical pressure by means of a movable ram on the foamable polymer composition to eject it from the holding zone through the die orifice into the zone of lower pressure, and 4) allowing the ejected foamable polymer composition to expand to form the foam.

A continuous process involves forming a foamable polymer composition and then expanding that foamable polymer composition in a non-stop manner. For example, prepare a foamable polymer composition in an extruder by heating a polymer resin to form a molten resin, blending into the molten resin a blowing agent composition at an initial pressure to form a foamable polymer composition, and then extruding that foamable polymer composition through a die into a zone at a foaming pressure and allowing the foamable polymer composition to expand into a foam. Desirably, cool the foamable polymer composition after addition of the blowing agent and prior to extruding through the die in order to optimize foam properties. Cool the foamable polymer composition, for example, with heat exchangers.

Foams of the present invention can be of any form imaginable including sheet, plank, rod, tube, beads, or any combination thereof. Included in the present invention are laminate foams that comprise multiple distinguishable longitudinal foam members that are bound to one another.

In another embodiment, the present invention relates to blowing agent combinations containing Z and E stereoisomers of hydrofluoroolefins as described herein for use in preparing foams. In other embodiments the invention provides foamable compositions, and preferably polyurethane, polyisocyanate and thermoplastic foam compositions, and method of preparing foams. In such foam embodiments, one or more of the present hydrofuoroolefins with stabilizer combinations are included as a blowing agent in foamable compositions, which composition preferably includes one or more additional components capable of reacting and foaming under the proper conditions to form a foam or cellular structure. Any of the methods well known in the art may be used or adapted for use in accordance with the foam embodiments of the present invention.

The present invention further relates to a method of forming a foam comprising: (a) adding to a foamable composition a combinations containing Z and E stereoisomers of hydrofluoroolefins of the present invention; and (b) reacting the foamable composition under conditions effective to form a foam.

3. Aerosol Propellants:

Another embodiment of the present invention relates to the use of the combinations containing Z and E stereoisomers of hydro fluoroolefins as described herein for use as propellants in sprayable compositions. Additionally, the present invention relates to a sprayable composition comprising the combinations containing Z and E stereoisomers of hydrofluoroolefins as described herein. The active ingredient to be sprayed together with inert ingredients, solvents and other materials may also be present in a sprayable composition. Preferably, the sprayable composition is an aerosol. Suitable active materials to be sprayed include, without limitations, cosmetic materials, such as deodorants, perfumes, hair sprays, cleaners, and polishing agents as well as medicinal materials such as anti-asthma and anti-halitosis medications.

The present invention further relates to a process for producing aerosol products comprising the step of adding combinations containing Z and E stereoisomers of hydrofluoroolefins as described herein to active ingredients in an aerosol container, wherein said composition functions as a propellant.

A further aspect provides methods of suppressing a flame, said methods comprising contacting a flame with a fluid comprising a combinations containing Z and E stereoisomers of hydrofluoroolefins of the present invention. Any suitable methods for contacting the flame with the present composition may be used. For example, a combinations containing Z and E stereoisomers of hydro fluoroolefins of the present invention may be sprayed, poured, and the like onto the flame, or at least a portion of the flame may be immersed in the flame suppression composition. In light of the teachings herein, those of skill in the art will be readily able to adapt a variety of conventional apparatus and methods of flame suppression for use in the present invention.

4. Fire Fighting Agents:

A further embodiment provides methods of extinguishing or suppressing a fire in a total-flood application comprising providing an agent comprising a combinations containing Z and E stereoisomers of hydrofluoroolefins of the present invention; disposing the agent in a pressurized discharge system; and discharging the agent into an area to extinguish or suppress fires in that area. Another embodiment provides methods of inciting an area to prevent a fire or explosion comprising providing an agent comprising a combinations containing Z and E stereoisomers of hydrofluoroolefins of the present invention; disposing the agent in a pressurized discharge system; and discharging the agent into the area to prevent a fire or explosion from occurring.

The term "extinguishment" is usually used to denote complete elimination of a fire; whereas, "suppression" is often used to denote reduction, but not necessarily total elimination, of a fire or explosion. As used herein, terms "extinguishment" and "suppression" will be used interchangeably. There are four general types of halocarbon fire and explosion protection applications. (1) In total-flood fire extinguishment, and/or suppression applications, the agent is discharged into a space to achieve a concentration sufficient to extinguish or suppress an existing fire. Total flooding use includes protection of enclosed, potentially occupied spaces such, as computer rooms as well as specialized, often unoccupied spaces such as aircraft engine nacelles and engine compartments in vehicles. (2) In streaming applications, the agent is applied directly onto a fire or into the region of a fire. This is usually accomplished using manually operated wheeled or portable units. A second method, included as a streaming application, uses a "localized" system, which discharges agent toward a fire from one or more fixed nozzles. Localized systems may be activated either manually or automatically. (3) In explosion suppression, a combination containing Z and E stereoisomers of hydrofluoroolefins of the present invention is discharged to suppress an explosion that has already been initiated. The term "suppression" is normally used in this application because the explosion is usually self-limiting. However, the use of this term does not necessarily imply that the explosion is not extinguished by the agent. In this application, a detector is usually used to detect an expanding fireball from an explosion, and the agent is discharged rapidly to suppress the explosion. Explosion suppression is used primarily, but not solely, in defense applications, (4) In inertion, a combination containing Z and E stereoisomers of hydrofluoroolefins of the present invention is discharged into a space to prevent an explosion or a fire from being initiated. Often, a system similar or identical to that used for total-flood fire extinguishment or suppression is used. Usually, the presence of a dangerous condition (for example, dangerous concentrations of flammable or explosive gases) is detected, and combination containing Z and E stereoisomers of hydro fluoroolefins of the present invention is then discharged to prevent the explosion or fire from occurring until the condition can be remedied.

The extinguishing method can be carried out by introducing the composition into an enclosed area surrounding a fire. Any of the known methods of introduction can be utilized provided that appropriate quantities of the composition are metered into the enclosed area at appropriate intervals. For example, a composition can be introduced by streaming, e.g. using conventional portable (or fixed) fire extinguishing equipment; by misting; or by flooding, e.g., by releasing (using appropriate piping, valves, and controls) the composition into an enclosed area surrounding a fire. The composition can optionally be combined with an inert propellant, e.g., nitrogen, argon, decomposition products of glycidyl azide polymers or carbon dioxide, to increase the rate of discharge of the composition from the streaming or flooding equipment utilized.

Preferably, the extinguishing process involves introducing a combination containing Z and E stereoisomers of hydro fluoroolefins of the present invention to a fire or flame in an amount sufficient to extinguish the fire or flame. One skilled in this field will recognize that the amount of flame suppressant needed to extinguish a particular fire will depend upon the nature and extent of the hazard. When the flame suppressant is to be introduced by flooding, cup burner, test data is useful in determining the amount or concentration of flame suppressant required to extinguish a particular type and size of fire.

5. Solvent:

The ideal hydrofluoroolefin, suitable for solvent applications, should have bp between 21-60° C. The product should be chemically stable in contact with metals, doesn't swell upon exposure to various plastic such as acrylonitrile butadiene styrene, PVC, polybutyelene tetraphathlate, polyethylene HD, polyethylene LD, polymethyle methacrylate, polyethylene, high impact polystyrene, polystyrene crystals, polystyrene 1160, polypropylene, polyamide 11, polycarbonate, polyvinylidene fluoride, polyetehrer block amide; or elastomeric material such as styrene butadiene 6510, ethylene propylene EP710, hydrogenated nitrile7DT1566, polychloroprene N658, polyacrylates DA 65, hyplalon DH70, fluorocarbon df, nitrile PB701, silicone SL1002, polyisoprene polybutadiene C6514, Teflon 62945R.

For all the application described in this invention, the compositions containing a combination of Z and E stereoisomers of hydrofluoroolefin, could be use in combination with a stabilizer or stabilizers selected from free radical scavengers, acid scavengers, oxygen scavengers, polymerization inhibitors, corrosion inhibitors and combinations thereof.

What is claimed is:

1. A method of preparing a combination of Z and E isomers of 1-chloro-3,3,3-trifluoropropene (R1233zd) comprising less than about 30% by weight of the Z isomer from a combination having more than about 30% by weight of the Z isomer comprising distillation of a combination of Z and E isomers of R1233zd having more than about 30% by weight of the Z isomer, wherein no solvent is added to the distillation process.

* * * * *